(12) United States Patent
Terao (10) Patent No.: US 8,979,879 B2
(45) Date of Patent: *Mar. 17, 2015

(54) NUCLEUS CHOPPER AND SPLITTER

(75) Inventor: Kenichi Terao, Tokyo (JP)

(73) Assignee: Asico, LLC., Westmont, IL (US)

(*) Notice: Subject to any disclaimer, the term of this patent is extended or adjusted under 35 U.S.C. 154(b) by 262 days.

This patent is subject to a terminal disclaimer.

(21) Appl. No.: 13/590,161

(22) Filed: Aug. 20, 2012

(65) Prior Publication Data

US 2013/0211414 A1   Aug. 15, 2013

Related U.S. Application Data

(63) Continuation-in-part of application No. 11/069,774, filed on Mar. 1, 2005, now Pat. No. 8,262,682.

(60) Provisional application No. 60/600,673, filed on Aug. 10, 2004.

(51) Int. Cl.
| | |
|---|---|
| *A61B 17/32* | (2006.01) |
| *A61F 9/007* | (2006.01) |
| *A61B 17/3209* | (2006.01) |
| *A61B 17/3211* | (2006.01) |
| *A61B 17/30* | (2006.01) |
| *A61B 17/295* | (2006.01) |
| *A61B 17/00* | (2006.01) |

(52) U.S. Cl.
CPC ......... *A61F 9/00754* (2013.01); *A61B 17/3209* (2013.01); *A61B 17/3211* (2013.01); *A61F 9/00736* (2013.01); *A61B 17/30* (2013.01); *A61B 2017/305* (2013.01); *A61B 17/295* (2013.01); *A61B 2017/00353* (2013.01)
USPC ........................................ 606/170

(58) Field of Classification Search
USPC .................. 606/166, 167, 170, 174
See application file for complete search history.

(56) References Cited

U.S. PATENT DOCUMENTS

| | | | | |
|---|---|---|---|---|
| 4,497,320 | A * | 2/1985 | Nicholson et al. | 606/79 |
| 5,167,618 | A * | 12/1992 | Kershner | 604/22 |
| 5,281,230 | A * | 1/1994 | Heidmueller | 606/127 |
| 5,290,302 | A * | 3/1994 | Pericic | 606/167 |
| 5,308,357 | A * | 5/1994 | Lichtman | 606/205 |
| 5,370,658 | A * | 12/1994 | Scheller et al. | 606/205 |
| 5,383,877 | A * | 1/1995 | Clarke | 606/148 |
| 5,400,768 | A * | 3/1995 | McNamara et al. | 600/104 |
| 5,501,698 | A * | 3/1996 | Roth et al. | 606/205 |
| 5,749,886 | A * | 5/1998 | Abidin et al. | 606/182 |
| 5,893,873 | A * | 4/1999 | Rader et al. | 606/205 |
| 5,893,877 | A * | 4/1999 | Gampp et al. | 606/205 |
| 6,051,004 | A * | 4/2000 | Gill | 606/147 |
| 6,306,155 | B1 * | 10/2001 | Chandler et al. | 606/205 |
| 6,855,156 | B2 * | 2/2005 | Etter et al. | 606/205 |
| 6,908,476 | B2 * | 6/2005 | Jud et al. | 606/205 |
| 7,011,666 | B2 * | 3/2006 | Feinsod | 606/107 |
| 8,262,682 | B2 * | 9/2012 | Terao | 606/170 |

(Continued)

*Primary Examiner* — Ryan Severson
(74) *Attorney, Agent, or Firm* — Wood, Phillips, Katz, Clark & Mortimer (57) ABSTRACT

A surgical instrument for both chopping and splitting the nucleus of an eye has a handle housing a shaft mounted within a guide tube which slides into and out of the instrument to bring first and second jaws into and out of contact with one another. The jaws are planar and positioned approximately perpendicular with the axis of the handle. The bottom edges of the jaws are brought into alignment to form a cutting edge when the jaws are forced together, and separate to perform a splitting action within a cut when the jaws are moved apart.

14 Claims, 11 Drawing Sheets

(56) References Cited

U.S. PATENT DOCUMENTS

| | | | |
|---|---|---|---|
| 2001/0056286 A1* | 12/2001 | Etter et al. | 606/205 |
| 2002/0062131 A1* | 5/2002 | Gallo, Sr. | 606/167 |
| 2003/0093099 A1* | 5/2003 | Anthone | 606/166 |
| 2003/0120305 A1* | 6/2003 | Jud et al. | 606/205 |
| 2006/0036270 A1* | 2/2006 | Terao | 606/167 |
| 2013/0204283 A1* | 8/2013 | Terao | 606/167 |
| 2013/0211414 A1* | 8/2013 | Terao | 606/107 |

* cited by examiner

NUCLEUS CHOPPER AND SPLITTER

This is a continuation-in-part of application Ser. No. 11/069,774, filed Mar. 1, 2005, and entitled "Nucleus Chopper and Splitter" which claims priority from application Ser. No. 60/600,673, filed 10 Aug. 2004 and entitled "Nucleus Chopper and Splitter", both of which are hereby fully incorporated herein by reference

FIELD OF THE INVENTION

The present invention relates generally to surgical instruments used in opthalmological surgery and, more particularly, to an instrument which can perform both chopping and splitting operations as part of cataract removal.

BACKGROUND OF THE INVENTION

Phacoemulsification has come to be a technique of choice for the removal of damaged or diseased lenses from the eye. Commonly, such surgery is called for when a patient develops cataracts, a condition in which a portion of the eye lens becomes hard and opaque. Unless the damaged lens is removed and replaced with a properly selected artificial lens, blindness or severely impaired vision will result.

Phacoemulsification is the use of ultrasonic energy to emulsify the damaged lens and aspirate the resulting lens particles from the eye. One of the most significant advantages of the use of phacoemulsification is that the apparatus itself is small and can fit through a relatively small incision, resulting in less fluid leakage from the eye capsule and shorter patient recovery times. It is desirable to limit the amount of ultrasonic energy used as much as possible in order to minimize the risk of damage to eye tissue. Often, the lens nucleus (the hardest portion of the lens) is chopped or split into smaller pieces prior to or during phacoemulsification. Smaller pieces require less energy to emulsify, and this shortens the time during which ultrasonic energy is actually being created by the phacoemulsification apparatus.

Known fractionating techniques include making incisions into the lens and, thereafter, prying the incisions open to split the lens into halves or quarters. As an example, U.S. Pat. No. 5,147,368 (Brown) teaches and describes a nucleus splitter in the form of a forceps, the jaws of which are intended to be inserted into a groove or incision already cut in the nucleus. When the handle of the nucleus splitter is squeezed, the jaws are forced apart thereby prying apart the groove or incision or splitting or cracking the nucleus into fragments.

U.S. Pat. No. 4,428,748 (Peyman, et al.) teaches and describes a combined ultrasonic emulsifier and mechanical cutter for surgery. This device includes the typical components of a phacoemulsification apparatus, namely, an ultrasonically vibrated hollow needle and one or more aspiration ports through which the emulsified lens particles are drawn and evacuated from the eye capsule. Peyman, et al. also includes a rotary mechanical cutter formed in the tip of the apparatus to be used for cutting nuclear tissue.

U.S. Pat. No. 6,592,541 (Kurwa) teaches and describes an opthamological surgical instrument device and method of use in which the tip of a phacoemulsification needle is formed with a cutting edge which can be inserted into the nucleus for the purpose of making an incision. As described by the inventor, a nucleus cracker or pre-chopper is then required to split the nucleus after which the phacoemulsification instrument is reinserted and used to emulsify and aspirate the lens fragments.

As used throughout, the term "pre-chopping" refers to the opthalmological surgical technique of making a plunge cut directly downward into the nucleus in order to form a channel or incision. The term "chopping" refers to the technique of forming grooves or incisions in the eye by drawing an instrument having a cutting edge across the lens.

Figure 1:
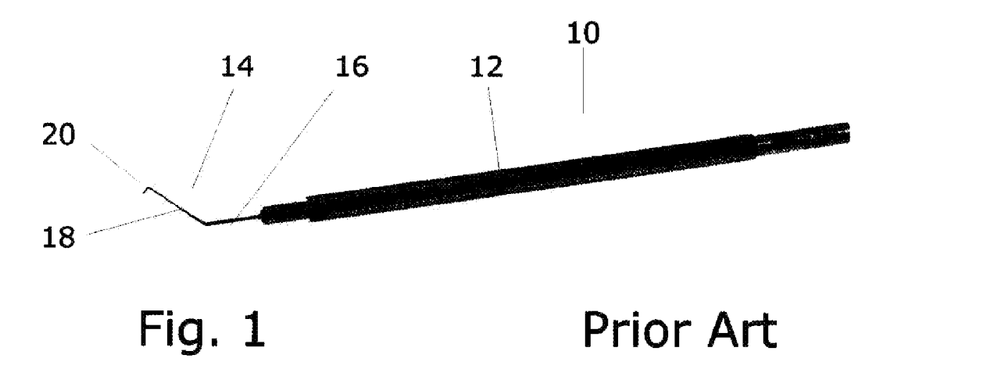
FIG. 1 is a perspective view of a first prior art chopper, ASICO Model AE-2515.
Figure 2:
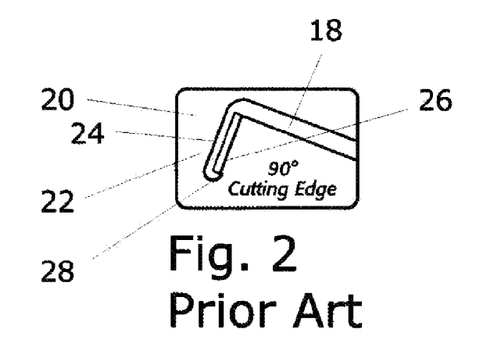
FIG. 2 is an enlarged view of the blade end of the chopper of FIG. 1 showing the blade with a 90 degree cutting edge.
Figure 3:
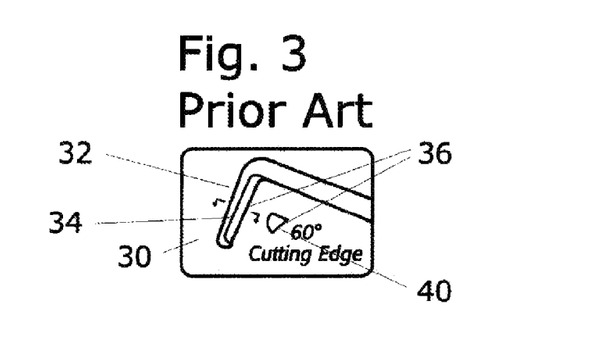
FIG. 3 is an enlarged view of the blade end of FIG. 1 showing the blade with a 60 degree cutting edge.

Examples of known prior art choppers are illustrated in the accompanying drawings. One such chopper identified as Model No. AE-2515 sold by ASICO LLC of Westmont, Ill. is shown in FIGS. 1, 2 and 3 and consists of an elongated shaft having a blade portion formed at the end of the shaft and extending at an angle to the shaft. The cutting edge of the blade portion faces toward the handle of the instrument, meaning an incision is made when the instrument is placed on the nucleus and then drawn across the nucleus. This instrument is available in both 90 degree and 60 degree angled cutting edges.

Another prior art chopper is identified as Model No. AE-2523 manufactured by ASICO LLC and consists of an elongated shaft with a hook-like projection extending at an angle to the shaft. As with the Model AE-2515, a cutting edge is formed on the interior surface of the hook and cutting occurs when the chopper is drawn across the nucleus. The hook shape allows the Model AE-2523 to be used to manipulate the lens within the capsule. Thus, once a first incision is made, the lens may be rotated 90 degrees and a second incision made to divide the lens into four quadrants.

Figure 6:
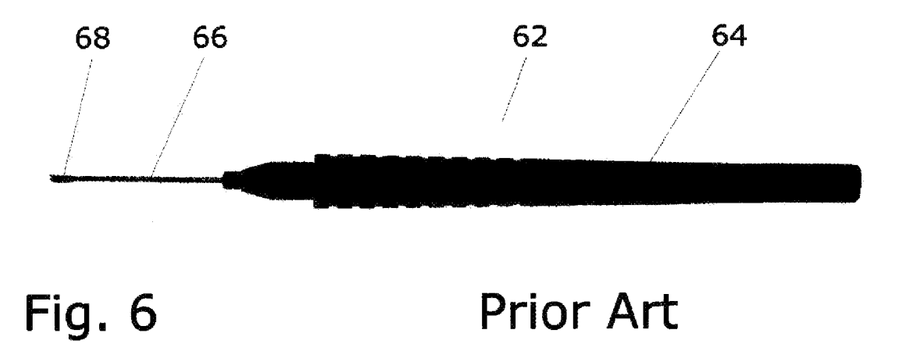
FIG. 6 is a perspective view of a prior art pre-chopper, ASICO Model AE-4287.
Figure 7:
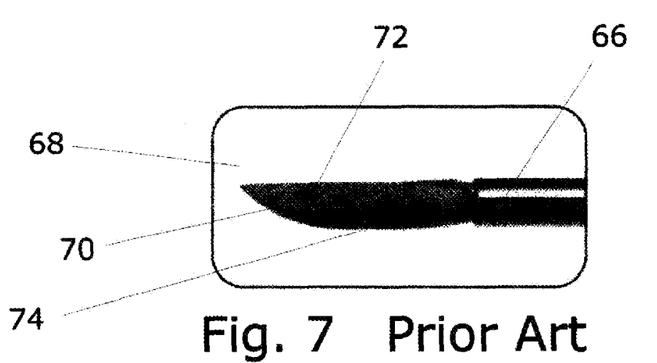
FIG. 7 is an enlarged view of the blade leaves of the pre-chopper shown in FIG. 6 shown in the closed position.
Figure 8:
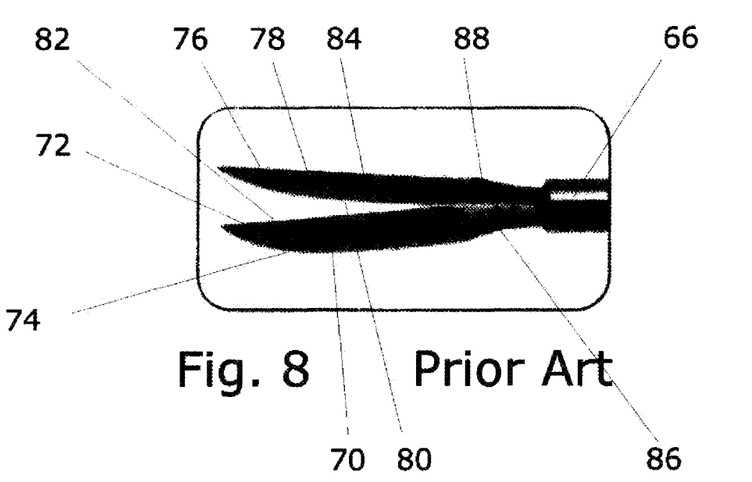
FIG. 8 is an enlarged view of the blade leaves of the pre-chopper shown in FIG. 6 shown in the separated position.

FIGS. 6, 7 and 8 show a prior art pre-chopper identified as Model No. AE-4287, sold by ASICO LLC. As described in more detailed herein, the Model AE-4287 has a spring steel blade assembly positioned within a tube with the end of the blade assembly forming a pair of blade leaves. The handle of the instrument is manufactured with a linkage which, in its normal position, is spread apart, a position in which the blade leaves are separated. When the handle is squeezed, the blade assembly is drawn into the blade tube and the two leaves are forced together to form a single solid blade. This blade has an upper straight surface which is sharpened and a lower curved surface which is blunt. In use, the AE4287 pre-chopper is inserted into the eye capsule and is rotated to bring the straight sharpened edge into contact with the upper surface of the lens. A plunge cut is then made to form a partial incision. The instrument is then turned 180 degrees to bring the blunt portion of the blade assembly into contact with the lens, within the incision. Thereafter, when the handle linkage is released, the leaves separate exerting a splitting or cracking force on the lens along the incision made by the pre-chopper. After several such incisions are made, and the lens is fractionated, the lens fractions may be emulsified and removed by phacoemulsification.

An instrument combining the features of both a chopper and a splitter is described in my co-pending application Ser. No. 11/069,774, filed Mar. 1, 2005, which is incorporated herein and is depicted in FIGS. 6-18. This instrument is a pair of tips that can be separated to act as a splitter and, when drawn together, form a single, vertical cutting edge used by drawing the instrument across the nucleus to incise it.

BRIEF DESCRIPTION OF THE INVENTION

The present invention is a surgical instrument which both incises and splits the nucleus of a lens in a manner which does not require the use of a pre-chopper.

Pursuant to the present invention, and in accordance with the teachings of a preferred embodiment of the invention described above, a pair of spring steel segments are inserted into a metallic tube and may be drawn inwardly and outwardly along the tube axis responsive to the actuation of a handle linkage. Along most of its length, each spring steel segment has a constant cross sectional dimension and is identical in dimension to the mating spring steel segment. For the purposes of this description, the spring steel segment's assembly will be referred to as a having a left hand and a right hand segment which are mirror images of each other. Each segment has an inner and an outer surface and, when assembled, the inner surfaces abut one another.

In a first preferred embodiment, the distal end of each spring steel segment has a tip formed thereon consisting of a first ramped section formed on the outer surface and extending generally axially with the handle and a second depending segment having at least one sharpened edge.

As the spring steel segments are drawn inward axially into the tube, the ramped portions on the outer surfaces contact the inner surface of the tube and the tips are pressed together with the sharpened surface or surfaces each forming a single cutting blade.

In a second preferred embodiment, the tip of the instrument is formed with a pair of jaws one of which is movable with relation to the other. The jaws are formed as generally planar segments in register one with the other such that the edges of the segments register as well. The jaw segments extend generally perpendicularly to the axis of the instrument and have top lateral and bottom edges selected and which may be sharpened to form the cutting edges. With the cutting edges formed along the lateral edges, the instrument can be used in a side-to-side motion with the surgeon cutting across the nucleus rather than forming an incision by drawing the instrument toward him. The incision thus formed is generally perpendicular to the axis of the handle and when draw tips are separated they separate in a direction coaxial with the handle thereby separating the incision.

In use, after an incision has been made, the tip is placed in the incision and the handle is manipulated to force the blades to separate and exert a separating or cracking force along the length of the incision. Where required the first incision is deepened by subsequent additional passes of the tip until the incision is deep enough to allow the lens to be split by allowing the blade segments to separate. These steps can be repeated until the lens is successfully fractionated.

The size and shape of the blade ends is such that a relatively small incision along the order of 0.8 mm can be used to allow access to the lens.

While the following describes a preferred embodiment or embodiments of the present invention, it is to be understood that this description is made by way of example only and is not intended to limit the scope of the present invention. It is expected that alterations and further modifications, as well as other and further applications of the principles of the present invention will occur to others skilled in the art to which the invention relates and, while differing from the foregoing, remain within the spirit and scope of the invention as herein described and claimed. Where means-plus-function clauses are used in the claims such language is intended to cover the structures described herein as performing the recited functions and not only structural equivalents but equivalent structures as well. For the purposes of the present disclosure, two structures that perform the same function within an environment described above may be equivalent structures.

BRIEF DESCRIPTION OF THE DRAWINGS

The foregoing will become more apparent upon consideration of the accompanying drawing figures in which.

DETAILED DESCRIPTION OF THE DRAWINGS

Referring now to FIG. 1, the numeral 10 indicates generally a first prior art chopper having a solid metallic body 12 from which a chopper blade 14 extends. As seen in FIG. 1, blade 14 has a first segment 16 generally coaxial with handle 12 a second segment 18 angled with respect to first segment 16 and a blade tip 20.

Referring now to FIG. 2, blade tip 20 is shown in an enlarged view as having a depending blade segment 22 extending at generally right angles to second blade segment 18. Blade segment 22 has a lead surface 24 which is polished and rounded in shape and a trailing surface 26 formed as a cutting edge. Cutting edge 26 terminates in a rounded bottom 28, formed as a smooth surface to protect other tissue in the eye.

Referring now to FIG. 3, a second tip embodiment 30 is shown having a lead or distal edge 32 which is formed with a rounded and smoothed surface 34. Opposite surface 34, a cutting edge 36 is formed and the small sectional view shown in FIG. 3 demonstrates that cutting edge 36 is formed by the intersection of surfaces 38 and 40 at a 60° angle.

Figure 4:
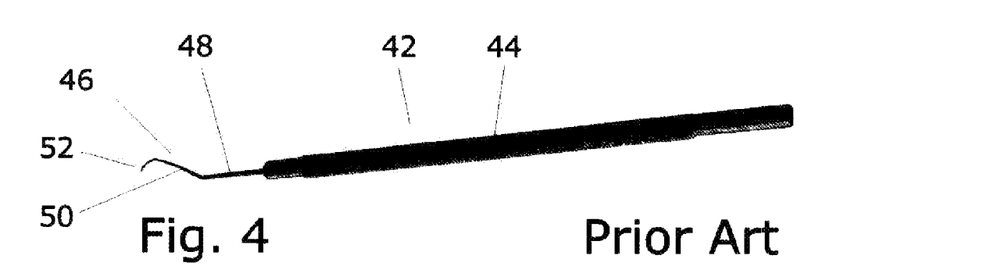
FIG. 4 is a perspective view of a second prior art chopper, ASICO Model AE-2523.
Figure 5:
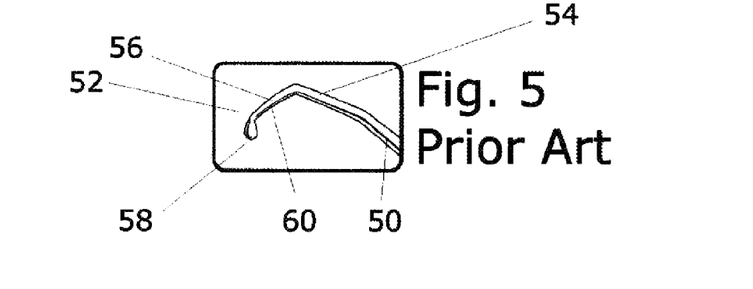
FIG. 5 is an enlarged view of the blade end of the chopper shown in FIG. 4.

Referring now to FIG. 4, a second prior art chopper 42 is shown, identified as ASICO Model AE-2523. Chopper 42 has a solid metallic handle 44 with a blade 46 extending therefrom. Blade 46 has a first segment 48 coaxial with handle 44, a second segment 50 extending at an angle to first segment 48 and a hook segment 52 which forms the terminus of segment 50. As seen in FIG. 5, hook segment 52 has a first hook segment 54 angled with respect to segment 50, a second hook segment 56 and a terminus 58. Terminus 58 is rounded and smoothed to protect any eye tissue with which it may come into contact from being cut. The trailing surface of second hook segment 56 has a cutting edge 60 formed thereon which performs the cutting or incising operation when chopper 42 is drawn across an eye lens.

Referring now to FIG. 6, the numeral 62 refers generally to a prior art pre-chopper identified above as ASICO Model AE-4287. Pre-chopper 62 has a handle assembly 64 to which is affixed a guide tube 66 from which protrudes a pre-chopper blade assembly 68. Blade assembly 68, while not shown herein in detail, comprises a pair of blade segments formed from spring steel which have a natural tendency to curl away from each other.

Referring now to FIG. 7, an enlarged view of pre-chopper blade assembly 68 is shown. Left hand leaf 70 is shown having an upper cutting edge 72 and a lower blunt edge 74 formed thereon. In this embodiment, sharp edge 72 is formed as a straight edge while blunt edge 74 is formed as a curved edge.

Referring now to FIG. 8, left blade leaf 70 is shown paired with right leaf 76. As with left leaf 74, right leaf 76 has an upper, sharpened surface 78 and a lower blunt surface 80. It should be understood that left leaf 70 and right leaf 76 are mirror images of each other and that the interior surface 82 of left leaf 70 is flat as is the interior surface of right leaf 84.

Also as seen in FIG. 8, left leaf 70 has a blade ramp 86 formed thereon and right blade leaf 76 has a mirror image ramp 88 formed thereon.

When handle 64 of pre-chopper 62 is unstressed, the left and right leaves 70, 76 are positioned apart as shown in FIG. 8. When handle 64 is squeezed, guide tube 66 is moved axially forward. When ramps 86, 88 come into contact with the interior surface of tube 66, leaves 70, 76 are forced inward towards each other until they abut as shown in FIG. 7. In this position, edges 72, 78 act as a single cutting edge while lower surfaces 74, 80 act as a single blunt surface.

Figure 9:
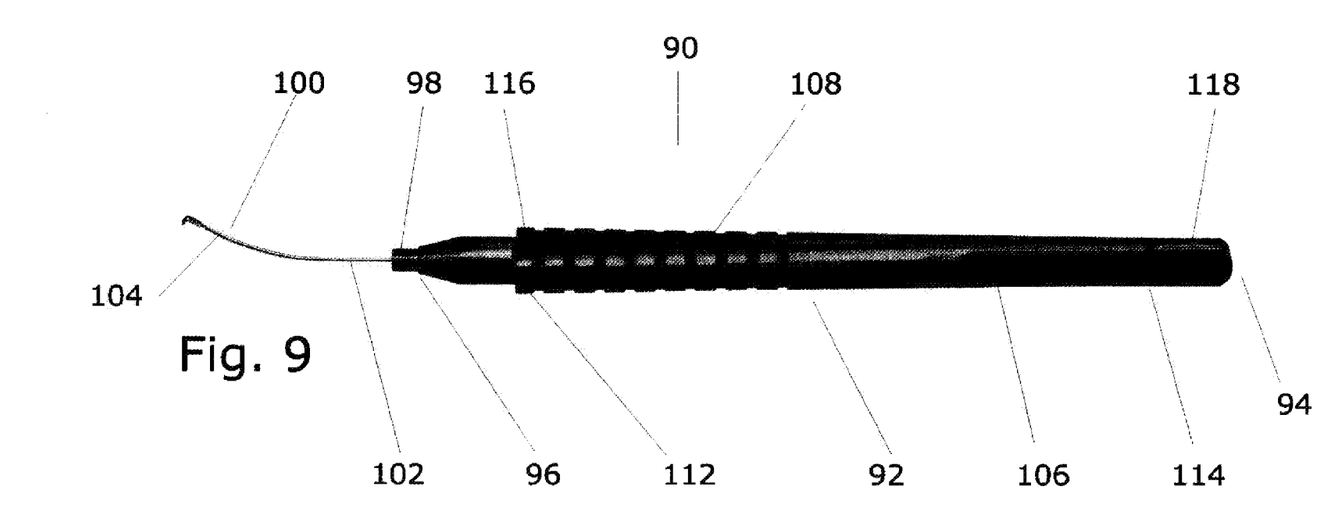
FIG. 9 is a perspective view of a preferred embodiment of the present invention.

Referring now to FIG. 9, the numeral 90 refers generally to an instrument for chopping and splitting lenses incorporating a preferred embodiment of the invention. Instrument 90 has a handle 92 with a distal end 94 and a proximal end 96. A mounting hub 98 is attached to handle 90 at proximal end 96. A guide tube 100 is slidably received through a central channel formed in hub 98, described in greater detail below. As shown in the embodiment of FIG. 9, guide tube 100 has a first, rectilinear segment 102 extending from hub 98 and a second curved segment 104 integral with segment 102.

Figure 10:
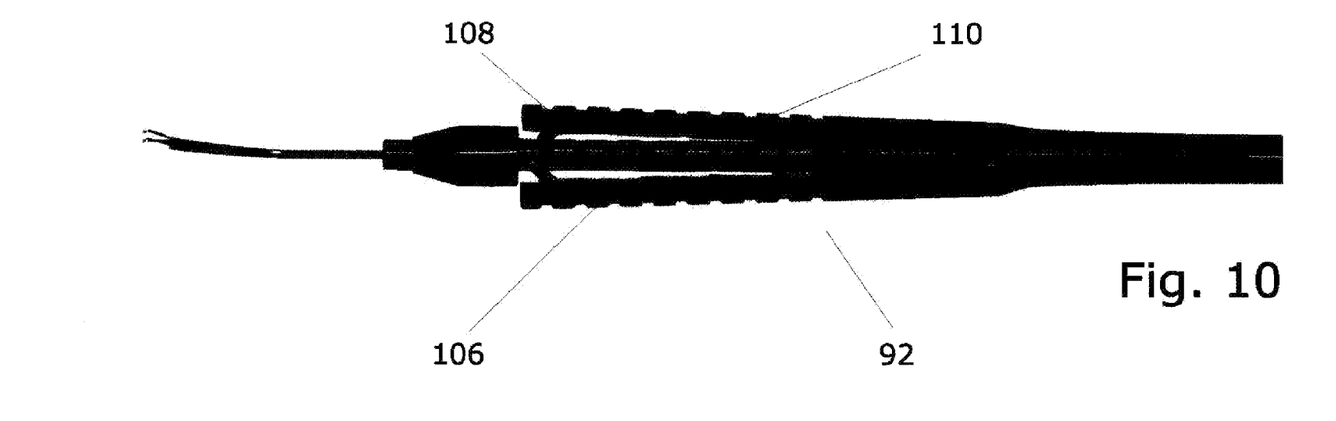
FIG. 10 is an enlarged view of a portion of the instrument shown in FIG. 9 showing the handle linkage in its open position.

Referring now to FIG. 10 handle 92 is shown having a left handle grip 106 and a right handle grip 108. Handle 92 also includes a central handle plate 110. As seen in FIG. 9, left handle grip 106 has a proximal end 112 and a distal end 114. Left handle grip 106 is attached to central handle plate 110 at distal end 114.

In like fashion, right handle grip 108 has a proximal end 116 and a distal end 118 and is attached to central handle plate 110 at distal end 118.

Preferably, left and right handle grips 106, 108 are formed from spring steel segments or segments having a natural spring such that when distal ends 114, 118 are attached to central handle plate 110, left and right handle grips 106, 108 bend away and are spaced apart from central handle plate 110. In other words, proximal ends 112, 116 when not gripped extend apart and away from central handle plate 110.

Figure 11:
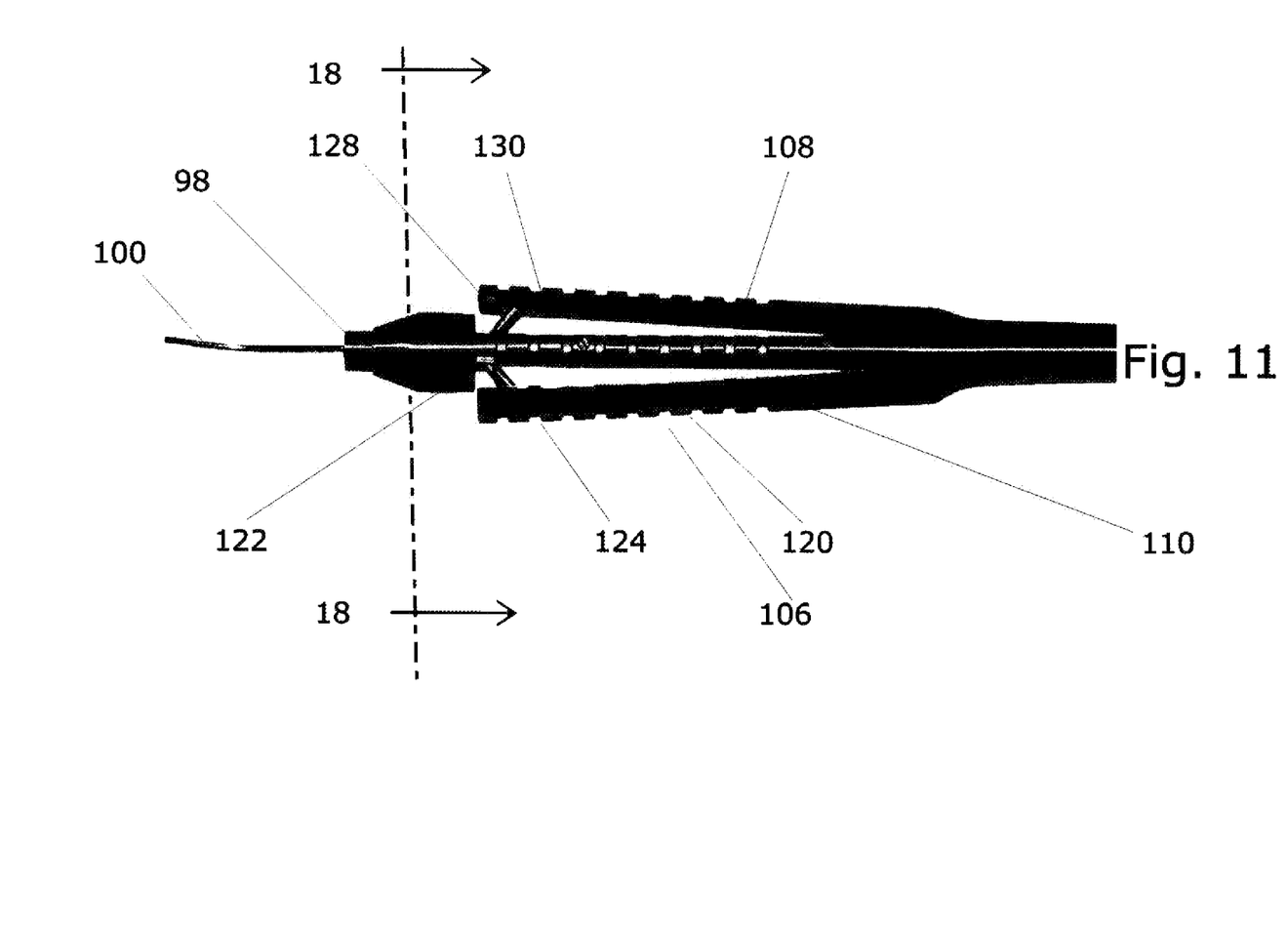
FIG. 11 is an enlarged view of a portion of the view of FIG. 10 showing the linkage in greater detail.

Referring now to FIG. 11, central handle plate 110 has a slider plate channel 120 formed therethrough proximate nib 98. A slider plate 122 is inserted into plate channel 120 and slides axially along channel 120 between the forwardmost and rearmost ends of channel 120. For the purposes of this description, the direction axially toward tube 100 will be referred to as the forward axial direction and movement axially toward distal end 94 will be referred to as the rearward direction.

As seen in FIG. 11, a left handle link 124 has two ends, one of which is pivotally attached to slider plate 122. The remaining end of left handle link 124 is slidably secured to left handle grip 106 as described below.

A right handle link 128 having two ends is pivotally secured at one end to slider plate 122 in the same manner as left handle link 124.

Right handle grip 108 has a right handle slider groove 130 formed therein, proximate end 116. As seen in FIG. 11, right handle line 128 is slidably secured at its other end within right hand slider groove 130. In identical fashion, left handle link 124 is secured within identical formed groove 126 (not shown) formed in left handle grip 106 proximate proximal end 112. Links 124, 128 are mechanically attached such that when left and right handle grips 106, 108 are gripped and moved toward central handle plate 110, slider plate 122 moves in an axially forward direction.

Figure 12:
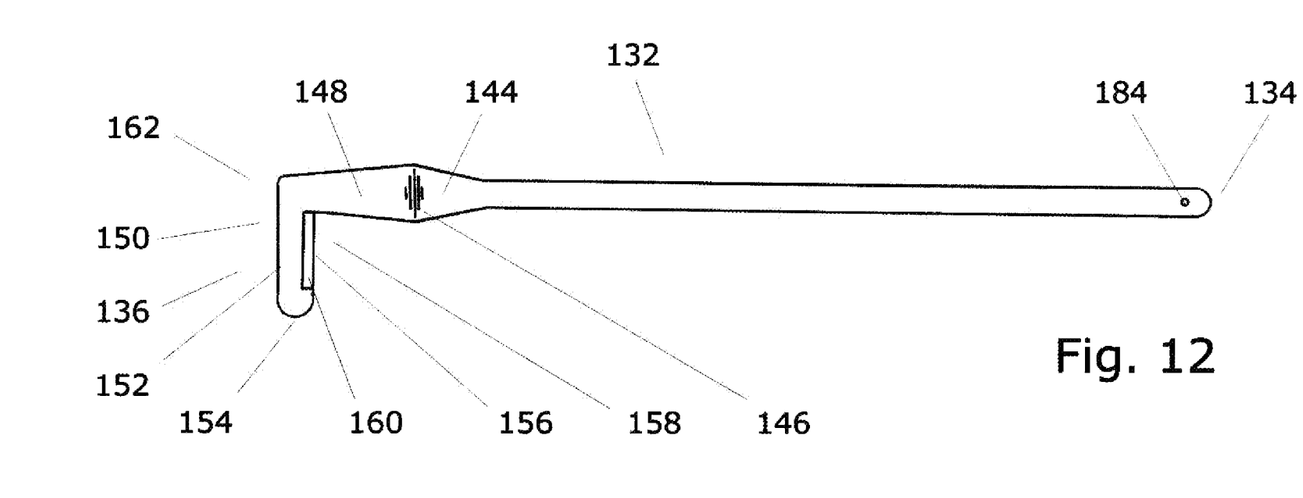
FIG. 12 is a lateral schematic view of a left blade segment.
Figure 13:
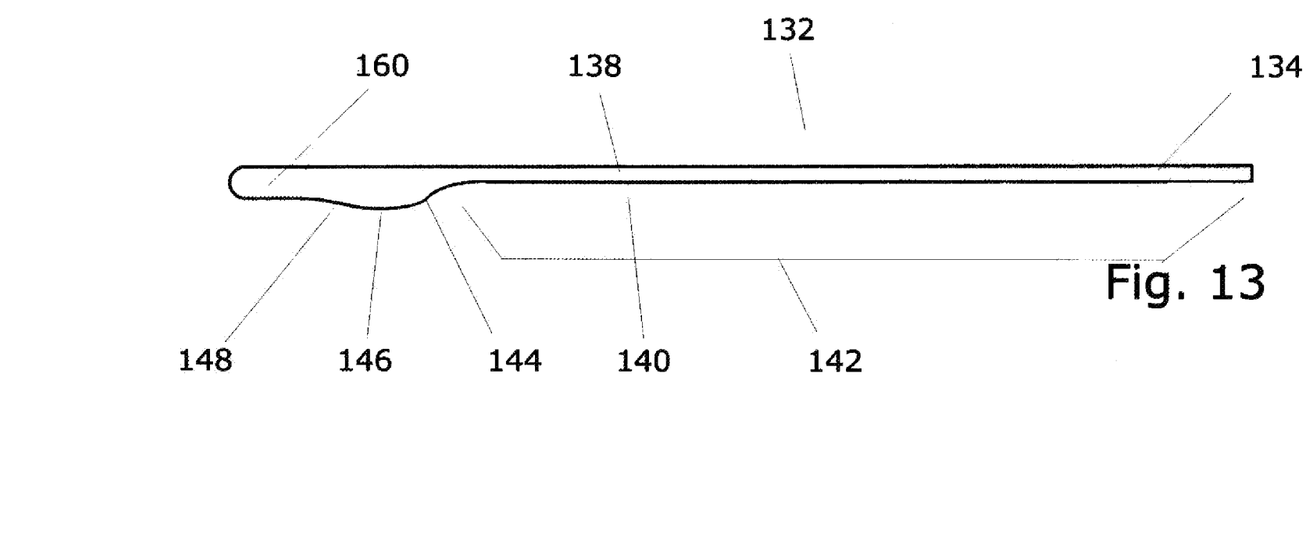
FIG. 13 is a top schematic view of the blade segment of FIG. 12.

Referring now to FIG. 12, a schematic lateral elevation of a left blade segment 132 is shown. Segment 132 is preferably formed from flat spring type surgical stainless steel. In this preferred embodiment, blade segment 132 has a distal end 134 and a proximal end 136. FIG. 13 is a top view of the blade segment 132 of FIG. 12. As seen, blade segment 132 has an interior surface 138 and an exterior surface 140. Interior surface 138 is formed as a flat surface throughout. External surface 140 is formed with a first flat segment 142 integrally formed with a ramp segment 144 which is progressively thicker in dimension than segment 142 until it reaches a maximum thickness at break 146. Thereafter, surface 140 tapers along segment 148 to proximal end 136.

Referring again to FIG. 12, distal end 136 is shown having a depending blade 150, depending from segment 148 at approximately a 90 degree angle. Blade 150 has a lead surface 152 which, in this preferred embodiment, is machined to be smooth and curved.

Blade 150 terminates in a bottom 154 which is also smooth and rounded. Blade 150 has a cutting edge 156 formed along a portion of trailing surface 158. In the embodiment shown, cutting edge 156 is shown by the intersection of angled surfaces 160, 162 which, in a preferred embodiment, meet at an angle of 90 degrees.

Segments 144, 146, 148 and 150 constitute left tip 162.

In this preferred embodiment, a right blade segment 164 is formed as a mirror image of left segment 132 and has a right inner surface 166. When assembled, left and right inner surfaces 138, 166 are in face-to-face contact along their respective lengths as described hereinafter.

Figure 14:
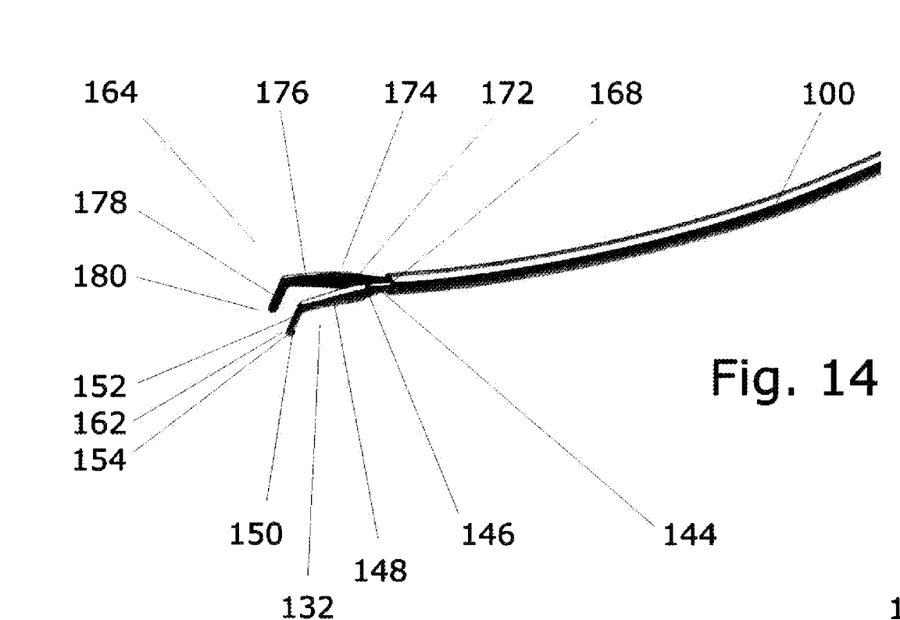
FIG. 14 is an enlarged view of the blade leaves extending from the blade tube shown in the open position.

Referring now to FIG. 14, a portion of guide tube 100 is shown with left and right blade segments 132, 164 slidably inserted therein. As shown in FIG. 14, the entire length of segment 142 is within tube 100. Protruding from tube end 168 is tip 162, including ramp segment 144, break 146, segment 148 and blade 150 of left blade segment 132. In similar fashion, segment 164 has a corresponding ramp segment 172, a corresponding break 174, a corresponding segment 176, and a corresponding blade 178 which collectively form right tip 180. It is to be understood that a right blade segment 170 corresponding to left blade segment 142 is also inserted within tube 100 in face to face contact with left segment 142.

Figure 15:
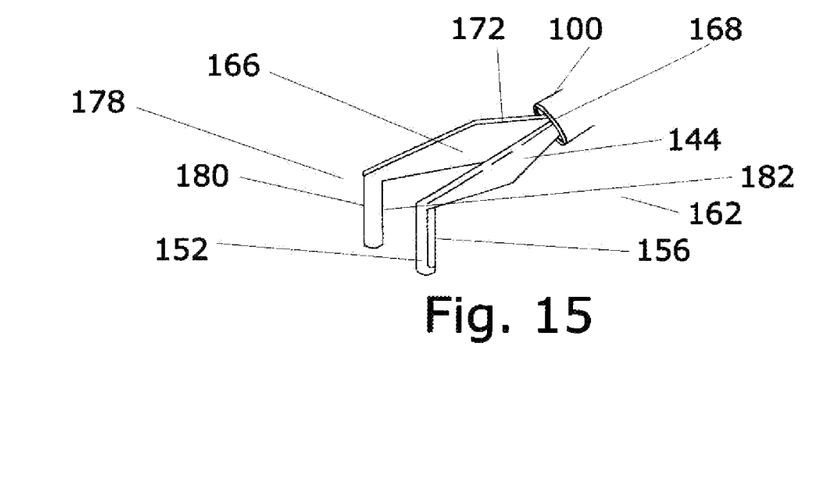
FIG. 15 is an enlarged detail of the blades shown in the open position.

Referring now to FIG. 15, an enlarged view of end 168 of tube 100 is shown with left and right lead surfaces 152, 180, left cutting edge 156 and a corresponding right cutting edge 182, a portion of right inner surface 166 and left and right ramps 144, 172.

In this preferred embodiment, left and right blade segments 132, 164 are secured to handle plate 110 and are held stationary with respect to instrument 90.

Figure 16:
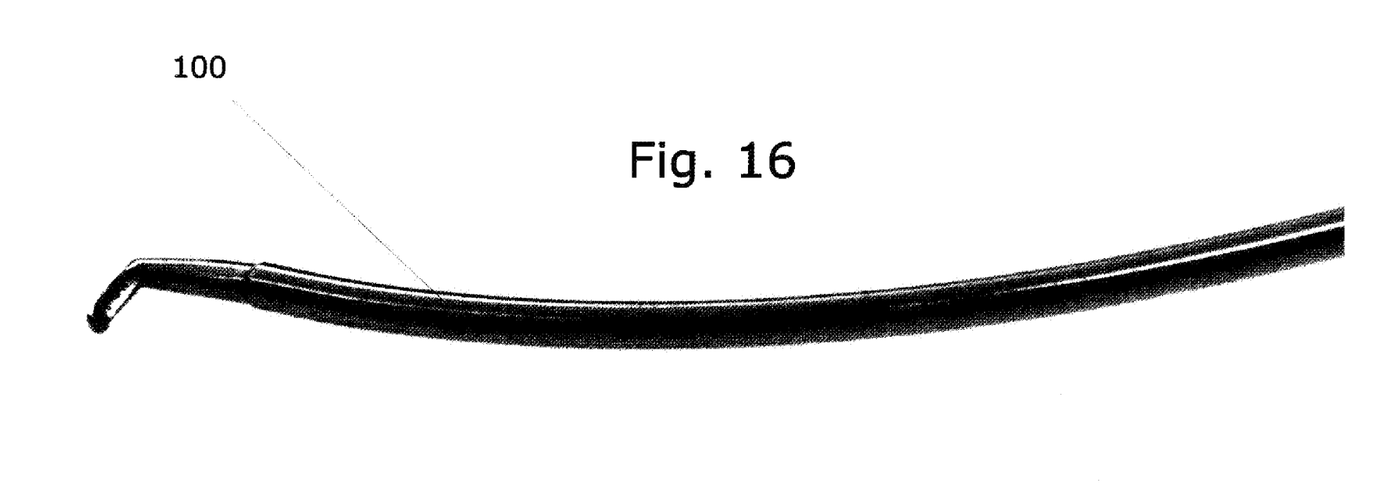
FIG. 16 is an enlarged perspective view of the blade leaves extending from the blade tube and shown in the closed position.

Referring now to FIG. 16, a portion of guide tube 100 is shown with guide tube 100 in its extended position as left and right handle segments 106, 110 are compressed to move slider plate 122 in an axially forward position. As shown in greater detail in FIG. 17, when left and right ramps 144, 172 contact guide tube 100, as slider plate 122 is being moved forward, left tip 162 is moved toward right tip 180 until inner surfaces 138, 166 are in contact along the entire length of blade segments 132, 164. When this occurs, left and right cutting edges 156, 182 are juxtaposed along their entire lengths to form, effectively a single cutting blade 192 as shown in FIG. 17.

Figure 18:
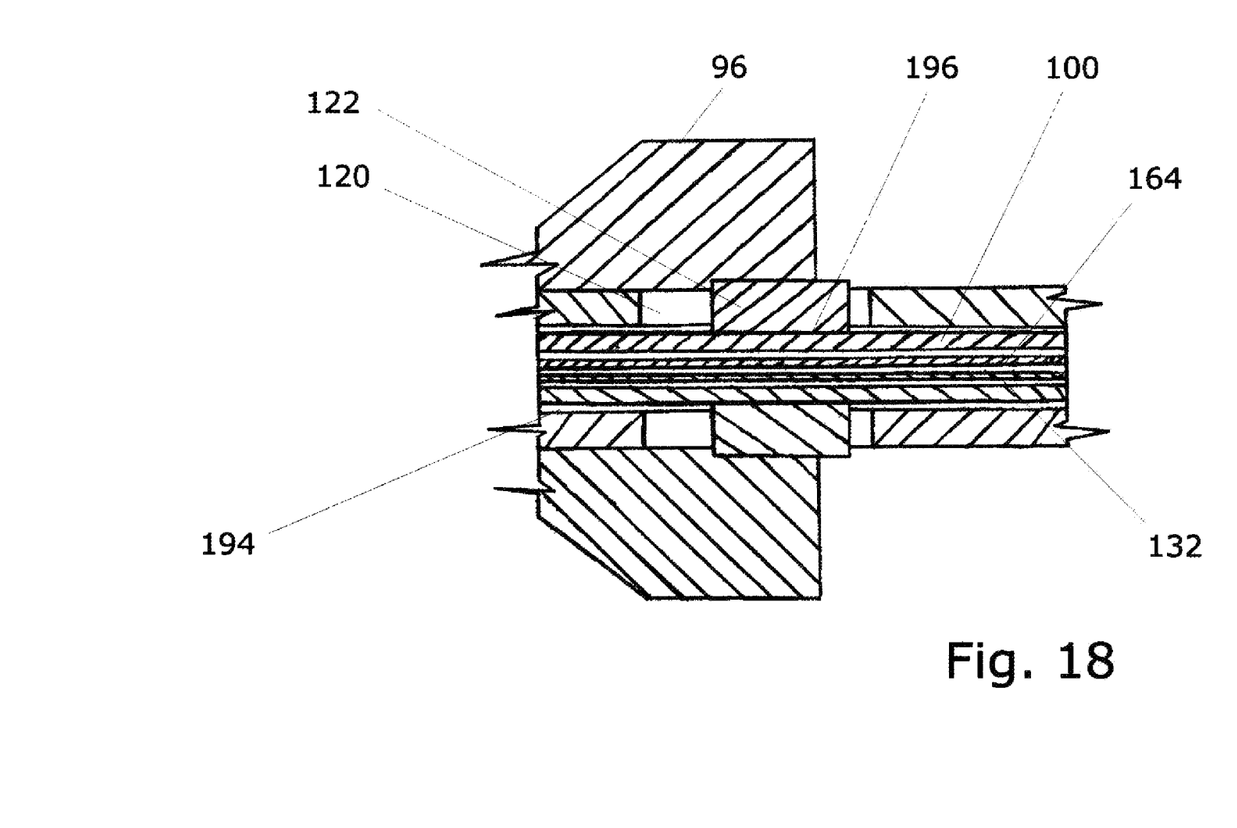
FIG. 18 is a partial sectional view taken along line 18-18 of FIG. 12.

Referring now to FIG. 18 a partial sectional schematic view of a preferred embodiment showing slider block 122 is shown. Hub 96 has a centrally positioned axial tube guide channel 194 formed therethrough. Slider block 122 has a central, axially extending tube mounting aperture 196 formed therethrough, within which guide tube 100 is received and gripped after it has been passed though aperture 194. Left and right spring steel segments 132, 164 are positioned within guide tube 100 and, because they are attached to handle plate 110 do not move when slider block 122 is moved in slot 120 to move guide tube 100 into or out of hub 96.

Figure 17:
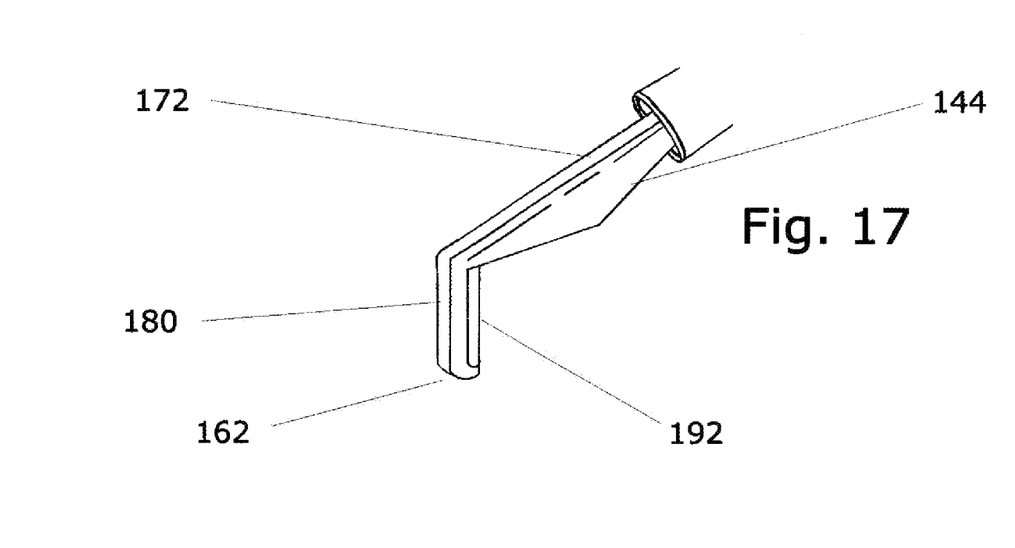
FIG. 17 is an enlarged detail of the blade leaves shown in the closed position.

As seen in FIGS. 16 and 17, with left and right handle grips 106, 108, compressed, instrument 90 may be used as a chopper by positioning blade 192 at a far end of the lens and drawing it across the lens to form a groove. After the groove is formed, blade 192 is positioned within the groove and the pressure on handle grips 106, 108 is controllably released to allow blade segments 132, 164 to again extend from guide tube 100 thereby separating tips 162, 180. When this occurs, surface segments 144, 146, 148 and 150 of left segment 132 and corresponding surfaces 172, 174, 176 and 178 of right segment 164 contact side walls of the groove and force the groove to widen. In this embodiment, the actions of chopping and "cracking" are repeated until the lens has separated into distinct segments.

When blade 192 is formed, it may also be used to manipulate and maneuver the lens into a position where a second cut may be made.

Figure 19:
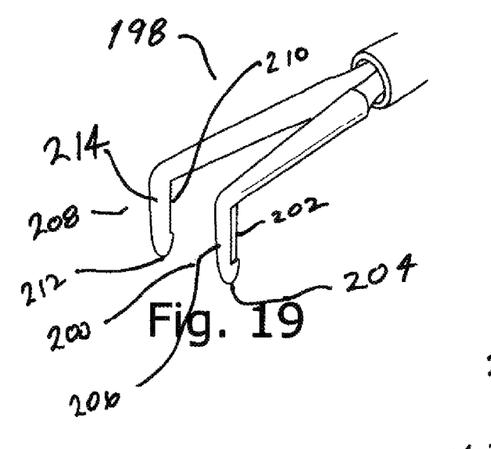
FIG. 19 is an enlarged detail of another type of blade having both lateral and bottom edges sharpened.

Referring now to FIG. 19, the numeral 198 identifies an instrument constructed in accordance with an embodiment of the present invention in which first tip segment 200 has a first, vertical sharpened edge 202 and a second sharpened edge 204 formed along the bottom of depending segment 206. In like fashion, second tip segment 208 has a vertical sharpened edge 210 and a lower sharpened edge 212 formed on depending segment 214.

When first and second tips 200, 208 are pressed together, edges 202, 210 form a single cutting edge as do edges 204, 212.

Figure 20:
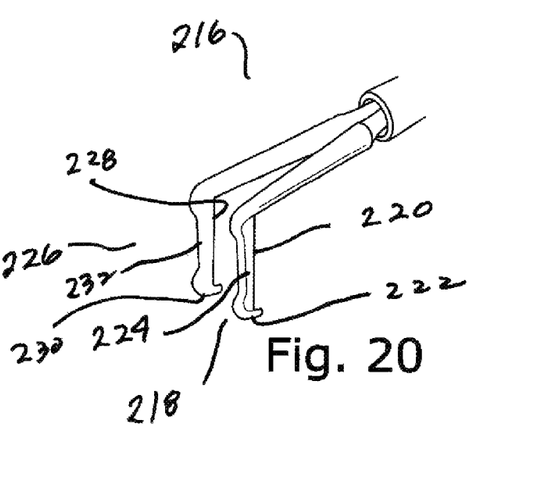
FIG. 20 is an enlarged detail of yet another configuration having an elongated vertical cutting edge.

Referring now to FIG. 20, the numeral 216 identifies another embodiment of the present invention in which first tip segment 218 has an elongated trailing edge 220 formed as a sharpened edge and terminates in a blunt foot 222 on tip segment 224. In like fashion, the second tip segment 226 has a trailing vertical elongated sharpened edge 228 terminating in a blunt foot 230 on tip segment 232.

When tip segments 218, 226 are drawn together, the trailing edges 220, 228 form an elongated cutting blade allowing for a deeper incision to be made with one pass.

Figure 21:
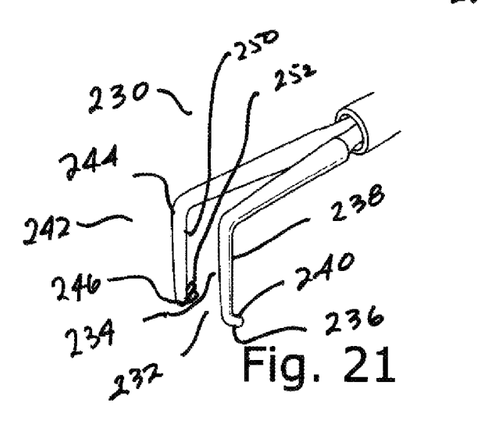
FIG. 21 is an enlarged detail of another blade configuration having vertical and angled sharpened edges.

Referring now to FIG. 21, the numeral 230 identifies yet another embodiment of the present invention having a first tip 232 having an elongated vertical segment 234, terminating in an angled segment 236 angled outwardly from segment 234. In the embodiment shown in FIG. 21, vertical edge 238 and angled edge 240 are sharpened. In like fashion, second tip 242 has a depending segment 244 terminating in an angled segment 246 having an opposite and equal angle to that of 240. Similarly, vertical edge 250 and angled edge 252 are sharpened.

When tips 232, 242 are pushed together, sharpened edges 238 and 250 are in registry and form a single cutting surface while cutting surfaces 240, 252 perform an undercut when moved across the lens.

Figure 22:
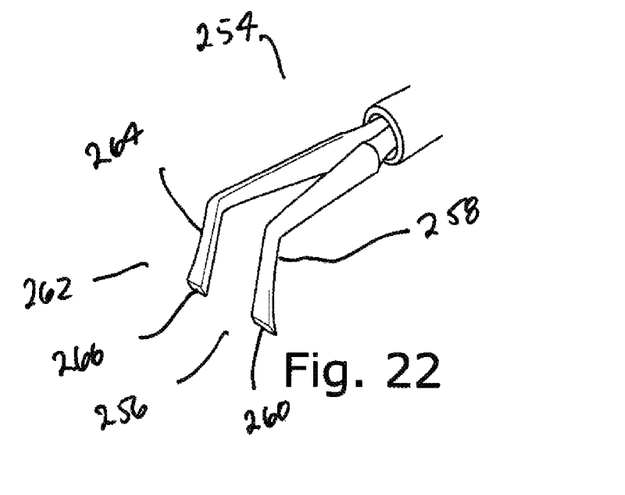
FIG. 22 is another enlarged detail of another blade configuration having sharpened lower edges.

Referring now to FIG. 22, the numeral 254 identifies another embodiment of the present invention in which a first tip 256 has an angled dependent segment 258 terminating in a lower sharpened edge 260. In like fashion, tip 262 has an identical depending segment 264 terminating in a sharpened bottom edge 266.

When tips 256, 262 are forced together, edges 260, 266 form a single horizontal cutting edge each can be used to perform a "plunge" cut into the lens.

The embodiment shown in FIGS. 19-22 have tips with a cracking or splitting action that takes place along a splitting axis that is substantially perpendicular to the axis of the instrument itself.

Figure 23:
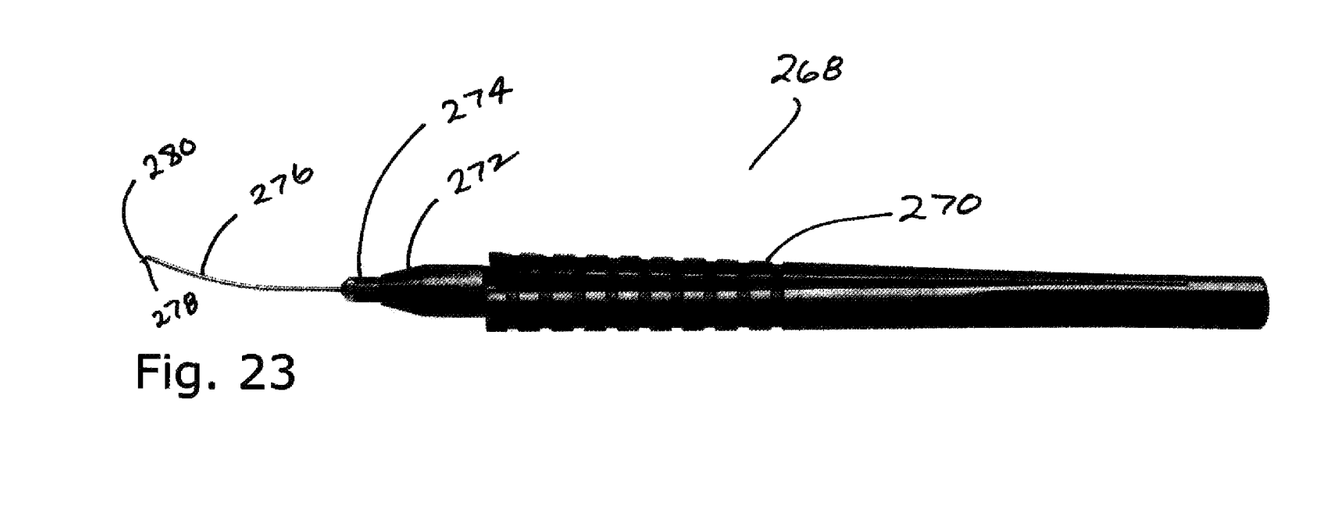
FIG. 23 is a perspective view of an instrument embodying a front-to-back splitting action.

Referring now to FIG. 23, another embodiment of the present invention is shown with the numeral 268 identifying a chopping/splitting instrument having a handle 270 constructed in the same fashion as the handles depicted and described in FIGS. 9, 10 and 11. Instrument 268 has a proximal end 272 within which a mounting hub 274 is attached. A guide tube 276 is slidably received through a central channel formed in hub 274 and terminates in a first jaw 278. A second jaw 280 is formed as the endmost segment of a shaft 282 as described below.

Figure 24:
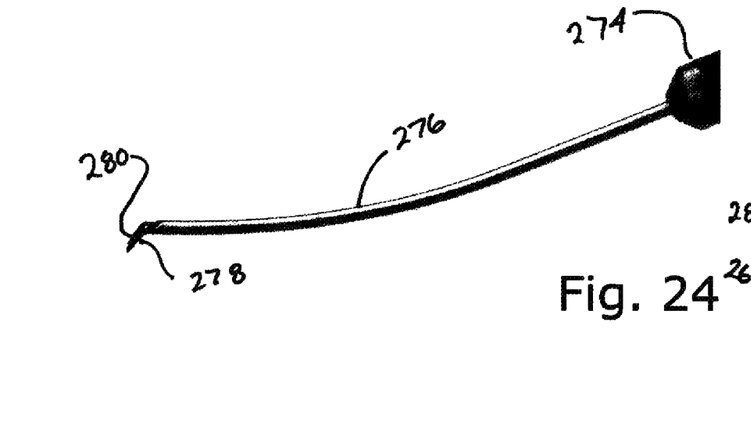
FIG. 24 is an enlarged view of the end of the instrument of FIG. 23 showing the tips in a closed position.

Referring now to FIG. 24, the tip end of instrument 268 is shown in greater detail. In particular, jaws 278, 280 are shown in the closed position wherein jaws 278, 280 are in contact with each other.

Figure 25:
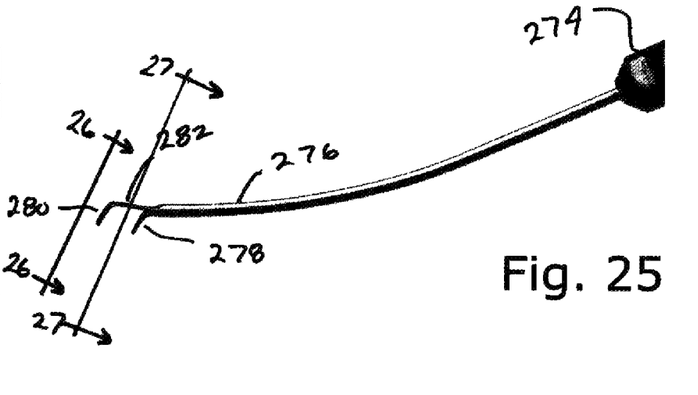
FIG. 25 is a view of FIG. 24 showing the tips in the opened position.

Referring now to FIG. 25, jaws 278, 280 are shown in an opened position with the endmost portion of shaft 282 shown extending outwardly from guide tube 276. In the embodiment shown in FIGS. 23, 24, 25, jaws 278, 280 are in the closed position when handle 270 is in the opened or unstressed position and are separated when handle 270 is squeezed to advance shaft 282 from guide tube 276.

It should also be understood that as described above, this linkage can be reversed so that an opposite action occurs, that is, where jaws 278, 280 are in the closed position and handle 270 is released.

Figure 26:
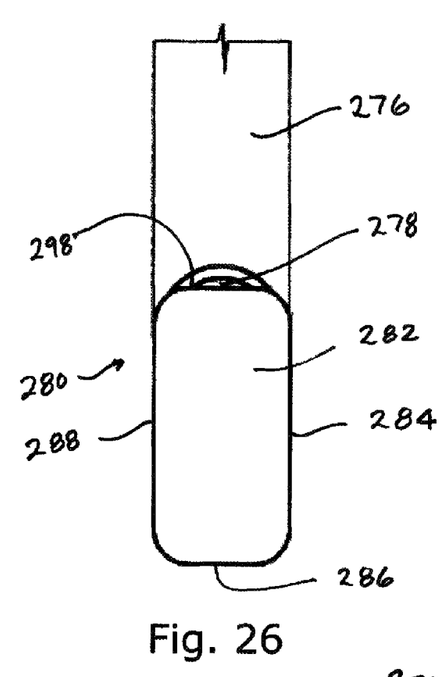
FIG. 26 is a view along 26-26 of FIG. 24.

Referring now to FIG. 26, an enlarged front view of jaw 280 is shown having a front face 282 formed in a flattened and paddle-like configuration. Jaw 280 has a first depending edge 284, a bottom edge 286, and a second depending edge 288 all or any one of which may be sharpened to create instruments with varying cutting capacities and characteristics.

Figure 27:
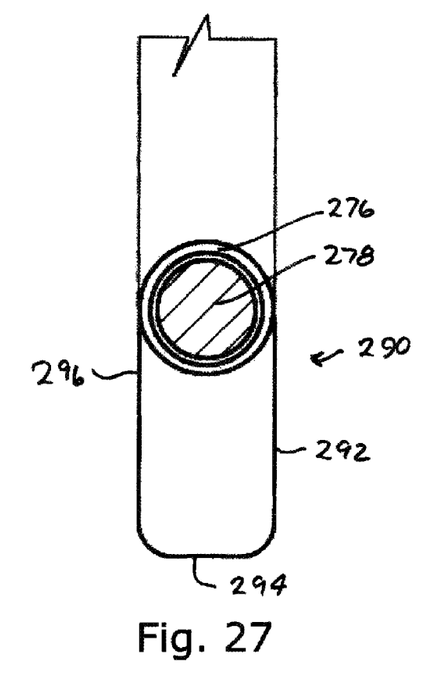
FIG. 27 is a view along 27-27 of FIG. 24.

Referring now to FIG. 27, rear jaw 290 is formed in a flattened and paddle-like configuration. In a preferred embodiment, those portions of front jaw 280 and rear jaw 290 that contact one another in the closed position, are congruent.

Rear jaw 290 has a first depending edge 292, a bottom edge 294, and a second depending edge 296 all or any of which may also be sharpened.

When front and rear jaws 280, 290 are in the closed position, edges 288, 296 are in registry as are edges 284, 292 and edges 286, 294. Where edges 288, 296 are sharpened, instrument 268 can perform a cut when edges 288, 296 are drawn across the lens. In like fashion, where edges 284, 292 are sharpened, instrument 268 will cut in a direction opposite that of edges 288, 296. Where both sets of edges are sharpened, the instrument will cut in both directions. Where edges 286, 294 are sharpened, instrument 268 may also be used as a plunge cutter. Where all edges are sharpened, instrument 268 may be used to plunge cut and then to perform a lateral cut in the direction of either edges 288, 296 or 282, 292.

It is also possible to sharpen an uppermost edge 298 of front jaw 280 and said edge can be used by turning the instrument to bring edge 298 in contact with the lens, as for example to sever a portion of the lens for removal.

In the embodiment show in FIG. 23, rear jaw 278 is fixed in position and front jaw 280 is movable in relation to rear jaw 278.

Figure 28:
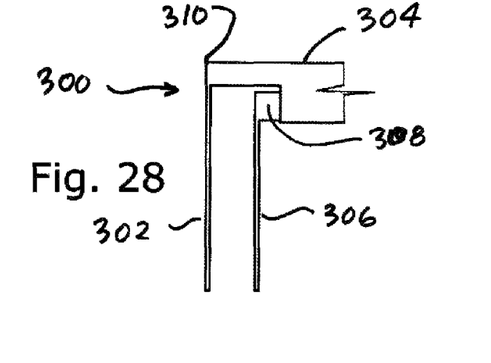
FIG. 28 is another embodiment of the instrument shown in FIG. 23 with the leading tip fixed in position and the trailing tip being axially adjustable.

Referring now to FIG. 28, the numeral 300 identifies an instrument formed in yet another embodiment of the present invention in which front jaw 302 is formed as a segment of guide tube 304 while rear jaw 306 is formed as an extension of shaft 308 which is slidably received by guide tube 304. Thus, front jaw 302 is fixed in position in relation to rear jaw 306 and rear jaw 306 is moved as described above by the actuation of the instrument handle.

As discussed in connection with FIGS. 26 and 27, the depending and lowermost surfaces of front and rear jaws 302, 306 may selectively be sharpened to produce instruments with different cutting characteristics and upper edge 310 of front jaw 302 may also be sharpened to allow instrument 300 to perform a cutting operation when the instrument is rotated.

As described above, a single instrument can be used for both chopping and splitting and can be constructed to allow chopping in a first direction and splitting in a direction generally perpendicular thereto, allowing a surgeon to choose by his or her own preference the direction in which the cut is to be made. Instruments constructed with a side-to-side splitting action are used to make cuts when the surgeon positions the cutting blades at the lens and moves the instrument either toward or away from him or her.

In an instrument with a front-to-back splitting action, the cutting edges are formed such that the surgeon can move his or her hand in a lateral motion to move the instrument across the lens and, thereafter, separate the jaws to perform a splitting or cracking in a direction generally perpendicular direction of the cut.

Thus, the procedures of chopping and cracking are accomplished through the use of a single instrument which, when inserted into the eye capsule, need not be removed until the chopping and splitting procedures have been completed. Once completed, the phacoemulsification instrument may be inserted and the chopped segments may be emulsified and aspirated in less time, using less energy than would be possible if the lens were not to be cracked.

What is claimed is:

1. A surgical instrument with an exposed cutting edge for cutting body tissue, said instrument comprising:
   a handle assembly,
   said handle assembly having a proximal end and a distal end,
   said handle assembly having an axis extending from said proximal end to said distal end;
   a first jaw extending from said handle assembly at said proximal end,
   said first jaw having a bottom edge,
   a second jaw extending from said handle assembly at said proximal end,
   said second jaw having a bottom edge,
   said second jaw being slidably moveable with respect to said first jaw;
   said handle assembly movable for: (i) selectively forcing said first and second jaws into contact with one another; and (ii) selectively forcing said first and second jaws apart from one another; and
   said first and second jaws sized and positioned to bring said jaws into face-to-face contact with said bottom edges aligned to form a single exposed and unenclosed cutting edge when said handle assembly is used to move said first and second jaws into contact one with one another,
   whereby said cutting edge can be used to form a cut in said body tissue and said first and second jaws can be used to widen said cut when said handle assembly is used to move said first and second jaws away from one another.

2. The surgical instrument as recited in claim 1 wherein said bottom edges are coextensive with one another when said first and second jaws are in contact with one another.

3. The surgical instrument as recited in claim 1 wherein said surgical instrument further comprises a mounting hub positioned at said handle assembly proximal end;
   a guide tube attached to and extending from said mounting hub;
   a shaft extending through and slidable within said guide tube,
   said shaft having first and second ends,
   said first shaft end attached to said handle assembly;
   said second shaft end attached to one of said first and second jaws, whereby activating said handle assembly causes said shaft to move within said guide tube to move at least one of said first and second jaws away from or toward the other of said first and second jaws.

4. The surgical instrument as recited in claim 3 wherein said handle assembly further comprises first and second handle grips pivotally attached to said handle assembly,
   said shaft attached to said first and second handle grips whereby moving said handle grips causes said shaft to move within said guide tube, thereby causing said first and second jaws to come into contact or to separate one from another.

5. The surgical instrument as recited in claim 4 wherein said first and second handle grips are biased to take a first, uncompressed position spaced apart from said handle assembly axis and are moveable toward said handle assembly axis to a second, compressed position.

6. The surgical instrument as recited in claim 5 wherein said first and second jaws separate as said handle grips are moved from said compressed position to said uncompressed position.

7. The surgical instrument as recited in claim 5 wherein said first and second jaws are brought into contact with one another when said handle grips are moved from said uncompressed to said compressed position.

8. The surgical instrument as recited in claim 5 wherein said first and second jaws separate as said handle grips are moved from said uncompressed position to said compressed position.

9. The surgical instrument as recited in claim 5 wherein said first and second jaws are brought into contact with one another when said handle grips are moved from said compressed to said uncompressed position.

10. The surgical instrument as recited in claim 3 wherein one of said first and second jaws extends from and is integral with said guide tube.

11. The surgical instrument as recited in claim 1 wherein said first and second jaws each have a side edge and said jaws are shaped and positioned such that said side edges align to form a single exposed and unenclosed cutting edge when said handle assembly is activated to force said first and second jaws into contact one with one another.

12. The surgical instrument as recited in claim 1 wherein said first and second jaws extend from said handle assembly proximal end at an angle that is substantially perpendicular to said handle assembly axis.

13. A method for chopping and splitting the nucleus of an eye, said method comprising the steps of:
   (a) providing a surgical instrument having a handle with a proximal end, a distal end, a handle axis extending between said proximal and distal ends, and first and second jaws slidably movable relative to one another each said jaw having a sharpened bottom edge which, when in contact with one another, form a cutting edge;
   (b) gripping said instrument to bring said jaws into contact to form said cutting edge;
   (c) pushing said cutting edge into said nucleus to make a first incision;
   (d) placing said first and second jaws within said incision;
   (e) moving said jaws apart from one another whereby said incision is widened to split said nucleus.

14. The method of claim 13 including the steps of:
   (f) drawing said cutting edge across said nucleus to deepen said incision; and
   (g) repeating steps (d) and (e).

\* \* \* \* \*